United States Patent
Quatieri, Jr. et al.

(10) Patent No.: US 10,127,929 B2
(45) Date of Patent: Nov. 13, 2018

(54) ASSESSING DISORDERS THROUGH SPEECH AND A COMPUTATIONAL MODEL

(71) Applicant: Massachusetts Institute of Technology, Cambridge, MA (US)

(72) Inventors: Thomas Francis Quatieri, Jr., Newtonville, MA (US); Gregory Alan Ciccarelli, Woburn, MA (US); Satrajit S. Ghosh, Wayland, MA (US); Christopher J. Smalt, Arlington, MA (US); James R. Williamson, Arlington, MA (US); Jeffrey Shane Palmer, Westford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/257,628

(22) Filed: Sep. 6, 2016

(65) Prior Publication Data
US 2017/0053665 A1   Feb. 23, 2017

Related U.S. Application Data

(63) Continuation-in-part of application No. 15/240,895, filed on Aug. 18, 2016, now abandoned.

(60) Provisional application No. 62/214,755, filed on Sep. 4, 2015, provisional application No. 62/207,259, filed on Aug. 19, 2015.

(51) Int. Cl.
*G10L 25/66* (2013.01)
*G10L 25/27* (2013.01)

(52) U.S. Cl.
CPC .............. *G10L 25/66* (2013.01); *G10L 25/27* (2013.01)

(58) Field of Classification Search
USPC .................................................. 704/236, 237
See application file for complete search history.

(56) References Cited

U.S. PATENT DOCUMENTS

| | | | |
|---|---|---|---|
| 2008/0208072 A1* | 8/2008 | Fadem | A61B 5/0484 600/544 |
| 2013/0040303 A1* | 2/2013 | Wang | C12Q 1/6883 435/6.12 |
| 2014/0303901 A1* | 10/2014 | Sadeh | G06F 19/22 702/19 |

(Continued)

OTHER PUBLICATIONS

D. Rudoy, D. N. Spendley, and P. Wolfe. Conditionally linear Gaussian models for estimating vocal tract resonances, *Proc. Interspeech*, 526-529, 2007.

(Continued)

*Primary Examiner* — Leonard Saint Cyr
(74) *Attorney, Agent, or Firm* — Hamilton, Brook, Smith & Reynolds, P.C.

(57) ABSTRACT

In a system and method for assessing the condition of a subject, control parameters are derived from a neurophysiological computational model that operates on features extracted from a speech signal. The control parameters are used as biomarkers (indicators) of the subject's condition. Speech related features are compared with model predicted speech features, and the error signal is used to update control parameters within the neurophysiological computational model. The updated control parameters are processed in a comparison with parameters associated with the disorder in a library.

22 Claims, 7 Drawing Sheets

(56) References Cited

U.S. PATENT DOCUMENTS

2015/0297106 A1* 10/2015 Pasley ............... A61B 5/0476
600/378
2016/0235352 A1* 8/2016 DiLorenzo ......... A61B 5/04001

OTHER PUBLICATIONS

D. Mehta, D. Rudoy, and P. Wolfe. Kalman-based autoregressive moving average modeling and inference for formant and antiformant tracking. *The Journal of the Acoustical Society of America*, 132(3), 1732-1746, 2012.

J. R. Williamson, T. F. Quatieri, B. S. Helfer, R. Horwitz, B. Yu, D. D. Mehta. Vocal biomarkers of depression based on motor incoordination. *AVEC 2013*.

J. Mundt, P. Snyder, M. S. Cannizaro, K. Chappie, and D. S. Geralts. Voice acoustic measures of depression severity and treatment response collected via interactive voice response (IVR) technology. *J. Neurolinguistics*, 20(1): 50-64, 2007.D.

T. F. Quatieri and N. Malyska. Vocal-Source Biomarkers for Depression: A Link to Psychomotor Activity. *Interspeech*, 2012.

A. Trevino, T. F. Quatieri, and N. Malyska., Phonologically-Based Biomarkers for Major Depressive Disorder. *EURASIP Journal on Advances in Signal Processing: Special Issue on Emotion and Mental State Recognition from Speech*, 2011(1), 1-18, 2011.

D. Sturim, P. Torres-Carrasquillo, T. F. Quatieri, N. Malyska, and A. McCree. Automatic Detection of Depression in Speech using Gaussian Mixture Modeling with Factor Analysis. *Interspeech*, 2011.

B. S. Helfer, T. F. Quatieri, J. R. Williamson, D. D. Mehta, R. Horwitz, and B. Yu. Classification of depression state based on articulatory precision. *Interspeech*, 2013.

Asgari, Meysam, Izhak Shafran, and Lisa B. Sheeber. "Inferring clinical depression from speech and spoken utterances." *Machine Learning for Signal Processing (MLSP), 2014 IEEE International Workshop on.* IEEE, 2014.

E. Tognoli and J. A. Scott Kelso. Brain coordination dynamics: True and false faces of phase synchrony and metastability. *Prog Neurobiol.* 87(1): 31-40, 2009.

S. L. Bressler, E. Tognoli, Operational principles of neurocognitive networks. *International Journal of Psychophysiology* 60:139-148, 2006.

Wiecki, Thomas V., Jeffrey Poland, and Michael J. Frank. "Model-Based Cognitive Neuroscience Approaches to Computational Psychiatry Clustering and Classification." *Clinical Psychological Science* 3.3 (2015): 378-399.

Tourville, Jason A, and Frank H Guenther. "The DIVA model: A neural theory of speech acquisition and production." *Language and Cognitive Processes* 26.7 (2011): 952-981.

King, Simon, et al. "Speech production knowledge in automatic speech recognition." *The Journal of the Acoustical Society of America* 121.2 (2007): 723-742.

15. i Livescu, Karen. Feature-based pronunciation modeling for automatic speech recognition. Diss. Massachusetts Institute of Technology, 2005.

Williamson, J.R., Bliss, D., Browne, D.W., and Narayanan, J.T., Seizure prediction using EEG spatiotemporal correlation structure. Epilepsy Behav., vol. 25, No. 2, pp. 230-238, 2012.

Boersma, Paul & Weenink, David (2015). Praat: doing phonetics by computer [Computer program]. http://www.praat.org/.

I. R. Titze and B. H. Story, "Rules for controlling low-dimensional vocal fold models with muscle activation," The Journal of the Acoustical Society of America, vol. 112, No. 3, pp. 1064-1076, 2002.

B. H. Story and I. R. Titze, "Voice simulation with a body-cover model of the vocal folds," The Journal of the Acoustical Society of America, vol. 97, No. 2, pp. 1249-1260, 1995.

M. Zañartu Salas "Influence of acoustic loading on the flow induced oscillations of single mass models of the human larynx," Ph.D. dissertation, Purdue University West Lafayette, 2006.

P. Geurts, D. Ernst, and L. Wehenkel, "Extremely randomized trees," Machine learning, vol. 63, No. 1, pp. 3-42, 2006.

Larson, Charles R., et al. "Interactions between auditory and somatosensory feedback for voice F 0 control." *Experimental Brain Research* 187.4 (2008): 613-621.

Gómez-Vilda, Pedro, et al. "Characterizing neurological disease from voice quality biomechanical analysis." Cognitive Computation 5.4 (2013): 399-425.

Gómez-Vilda, Pedro, et al. "Glottal source biometrical signature for voice pathology detection." *Speech Communication* 51.9 (2009): 759-781.

"DIVA Source Code" DIVAsimulink7-6. Boston University. http://www.bu.edu/speechlab/software/diva-source-code/.

Guenther, Frank H., Satrajit S. Ghosh, and Jason A. Tourville. "Neural modeling and imaging of the cortical interactions underlying syllable production." *Brain and language* 96.3 (2006): 280-301.

Ciccarelli, Gregory, Thomas Quatieri, Satrajit Ghosh. Neruophysiological Vocal Source Modeling for biomarkers of Disease. In Interspeech 2016, to appear.

Patel, Rupal, et al. ""The Caterpillar": A Novel Reading Passage for Assessment of Motor Speech Disorders." American Journal of Speech-Language Pathology 22.1 (2013): 1-9.

Fairbanks, Grant, ed. Voice and articulation: Drillbook. Harper & Brothers, 1940.

Darley, F. L., Aronson, A. E., Brown, J. R. (1975). Motor speech disorders. 3rd ed. Philadelphia, PA W.B. Saunders Company.

Van Riper, C. (1963). Speech correction. 4th ed. Englew000d Cliffs, NJ Prentice Hall.

Aesop (2016) The North Wind and the Sun. In. https://en.wikipedia.org/wiki/The_North_Wind_and_the_Sun.

Bishop, Christopher M. "Pattern recognition." Machine Learning 128 (2006).

Guenther, Frank H. (2016) "Neural Control of Speech" pp. 99-109 and Ch. 10 pp. 273-312.

Brian Harel, Nicole Reilly, Phillip Chappell, Peter J. Snyder "Voice acoustical measurement of the severity of major depression", (2004) pp. 30-35.

Gómez-Vilda, Pedro et al., "Phonation Biomechanics in Quantifying Parkinson's Disease Symptom Severity", (2016) pp. 93-102.

Oren Civier, et al., "Computational modeling of stuttering caused by impairments in a basal ganglia thalamo-cortical circuit involved in syllable selection and initiation", (Brian and Language 126 (2013) 263-278.

Gregory Ciccarelli, "Biomarkers derived from neurophysiological computational modeling", (2016) pp. 1-7.

Cummins, Nicholas et al. "A review of depression and suicide risk assessment using speech analysis", Speech Communication, vol. 71, Apr. 6, 2015, pp. 10-49.

International Search Report and Written Opinion, issued in International Application No. PCT/US2016/047609, entitled "Assessing Disorders Through Speech and a Computational Model," dated Nov. 17, 2016.

* cited by examiner

ASSESSING DISORDERS THROUGH SPEECH AND A COMPUTATIONAL MODEL

RELATED APPLICATIONS

This application is a continuation-in-part of U.S. application Ser. No. 15/240,895, filed Aug. 18, 2016, which claims the benefit of U.S. Provisional Application 62/214,755, filed Sep. 4, 2015 and U.S. Provisional Application 62/207,259, filed on Aug. 19, 2015.

The entire teachings of the above applications are incorporated herein by reference.

BACKGROUND

Motivations for this invention are the many neurological, trauma, and cognitive stress conditions that can alter motor control and cognitive state and therefore alter speech production and other sensorimotor activities by influencing the characteristics of the vocal source, tract, and prosodics, as well as other motor components. Early, accurate detection of such conditions aid in possible intervention and rehabilitation. Thus, simple noninvasive biomarkers are desired for determining severity. Recently, there have been significant efforts in the use of vocal biomarkers [3]-[9]. Features may be extracted from speech and compared to a library of such features for various disorders to diagnose or predict severity of the disorder.

SUMMARY OF THE INVENTION

In an automated system for assessing a condition of a subject, speech features are extracted from data from a subject. The extracted speech features are compared to predicted speech features from a neurophysiological computational model to obtain an error signal. The error signal is inverted through an inverse of the neurophysiological computational model to update internal parameters of the neurophysiological computational model.

The updated internal parameters may be applied to the model in multiple iterations of the steps of comparing, inverting and applying to obtain updated internal parameters to be processed. The process may additionally include further feature extraction from the updated internal parameters. For example, a correlation structure for the subject may be extracted from the updated internal parameters.

The extracted speech features and the predicted speech features may include representations of vocal source, representations of vocal tract and time series representations.

The subject may be accessed, for example, for a neurological disorder such as for depression, Parkinson's disease, traumatic brain injury, or the effects of cognitive stress. The neurophysiological computational model may be a muscular control model and the internal parameters may be control parameters.

Otherwise stated, in an automated system for assessing a condition of a subject, a speech-related signal of the subject is received and speech features are extracted from the speech related signal. The extracted speech features are compared to predicted speech features from a control model to obtain an error signal. The error signal is inverted through an inverse of the model to update control parameters of the model. The updated control parameters are processed in a comparison with parameters associated with the disorder in a library and the condition of the subject is assessed based on that comparison.

DETAILED DESCRIPTION OF THE INVENTION

Figure 1:
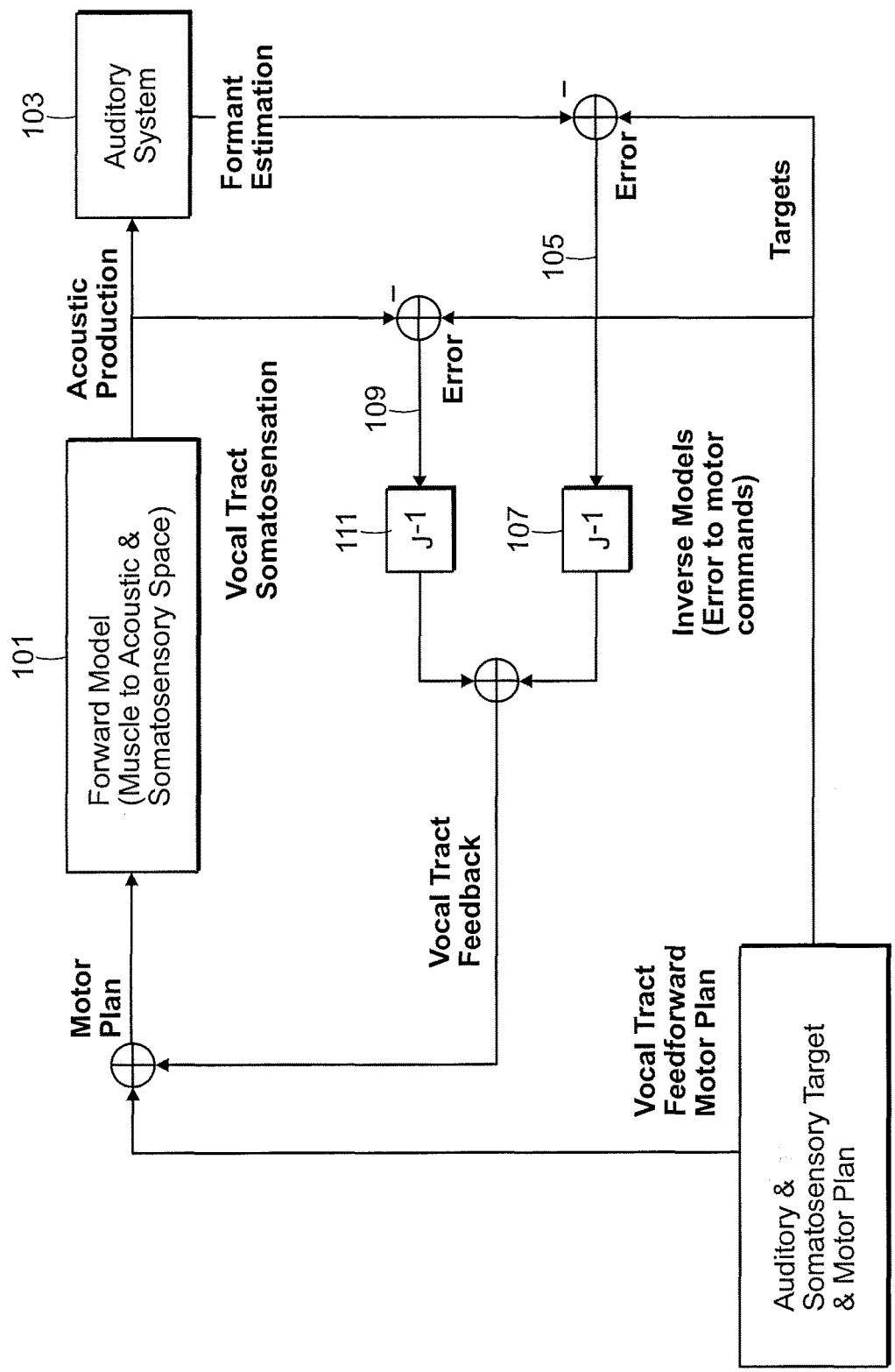
FIG. 1 illustrates a prior art DIVA neural computational control model which may be used in embodiments of the present invention.

A description of example embodiments of the invention follows.

A computational model is a set of parameterized equations that describe the working of a system (speech production, general motor control, knowledge acquisition, decision making, memory recall, performance). The parameters from a set of such equations are the new feature space for traditional data analysis tasks such as diagnosing or predicting severity of a disorder.

A distinguishing characteristic of the invention is the use of a neurophysiological computational model. A neurophysiological computational model is a specific instance of a computational model whose equations are anchored in the known or hypothesized neurophysiology of the subject. In particular, the computational model may describe control of muscles, such as used in speech, by the brain. For example, the mathematical components of a neurophysiological computational model may have hypothesized locations in the brain, and associated speech production-related, speech perception-related system regions, and the mathematical relationships between these components reflect biological relationships and interactions between the components. Consequently, the parameters in such a neurophysiological computational model have a concrete basis in the brain and components controlled by the brain. Because the model parameters have a definite neurobiological basis, we recognize that these parameters may be useful for assessing neurophysiological disorders. We recognize the utility offered by these parameters, which cannot be directly measured, and use these parameters within a system for assessing neurophysiological health. The neurophysiological computational model in this invention engages the speech production, speech perception control loop, and demonstrates how speech can be used to estimate the unobserved model parameters.

Model-based feature extraction serves several purposes: (1) It can provide greater insight into the system under investigation. Superior insight can enable targeted treatments, or approaches to task performance (e.g., methods of effectively training an individual, treating different aspects of a disorder, monitoring the effectiveness of an intervention) (2) It can support simulation of interventions and performance/risk reduction. Multiple courses of action (drug delivery, behavioral intervention, material presentation) can be tested in silico and the optimal one selected for an individual (3) It can provide an improved understanding of the system itself. This can lead to better models and the benefits of better models. (4) It can support individualization/personalization. A broad set of equations can be fit to a single subject in such a way that knowledge from many individuals inform the structure of the equations and knowledge of the individual tailors the equations to be person specific. Instead of one-size-fits all approaches to a person, interventions will be personalized.

Traditional approaches to feature extraction operate only on input data (e.g., speech, accelerometer, EEG signals, voxel based activations in brain activity). A model based approach fuses prior knowledge of the system with the input data. Fusion of a model with input data can constrain the space of predictions to realizable possibilities. Consequently, performance with model-based features may lead to better estimations and predictions than when only the raw data is used. Therefore, model-based features have a better probability of generalizing to different circumstances. Critically, the estimation of model parameters provides a window into the system under investigation without costly, invasive, or difficult to perform procedures. Model based approaches uniquely describe the inner workings of a subject in order for appropriate, personalized, optimal actions to be taken.

In this invention, we introduce multi-scale vocal features derived from neurophysiological computational models of speech production. One such model is the Directions into Velocities of Articulators (DIVA) model [13]. DIVA is a neural network model connecting acoustics, physiology, and neurophysiology. Given a behavioral (acoustic) measurement of speech, through an iterative learning process, the model computes parameters that correspond to different aspects of the speech production process including articulatory commands and auditory and somatosensory feedback errors. The DIVA system has been used to study speech generation, including speech disorders, as DIVA relates to the structure and function of the brain. The DIVA model is a magnetic resonance imaging (MRI)-validated neurocomputational model of speech production developed out of Boston University by Frank Guenther and colleagues [26]. The primary aim of the DIVA model was to provide a neurobiologically plausible, quantitative, system level description of low level speech motor control. The neurobiological plausibility follows from the validation of different aspects of the model correlating with different sensorimotor speech production and perception experiments conducted with functional MM (fMRI). DIVA is a quantitative model as it consists of a series of equations that describe the inputs, outputs, and processing of each functional block. DIVA models the brain at the systems level. It abstracts away biophysical details such as neurotransmitter binding kinetics or neuronal spike timing dynamics. Over DIVA's decades of development, DIVA has been used almost exclusively for explaining principles of low level speech motor control. DIVA hypothesizes that the brain has auditory and somatosensory targets when producing speech, and that there are feedforward and feedback mechanisms, embodied by DIVA's equations, that govern the movement of the speech articulators associated with the vocal tract (e.g., lips, tongue, and jaw). At no point prior to this work has DIVA been used as a tool for quantitative assessment of neurophysiological health for individual subjects.

FIG. 1 illustrates the DIVA model. A forward model represents the transformation from muscle to acoustic and somatosensory space during speech based on the collection of experimental data from human subjects performing the speech task. The DIVA system monitors the performance of speech characteristics, such as formants, resulting from operation of the forward model. The target formants resulting from actual speech of the subject are compared to the formant's predicted by the model to produce an error 105 that is applied back through an inverse model 107. The DIVA model also incorporates somatosensation as an output that can be compared to target somatosensation to produce an error 109 that is returned through an inverse model 111. The processed errors are combined to provide vocal tract feedback that modifies the motor plan, that is control parameters to the forward model. The control parameters are modified in a loop to reduce the error from the target signals. After multiple iterations, the updated control parameters define the control to the forward model that generates the target speech, allowing for study of speech generation.

Here, we recognize that the control parameters of DIVA represent a mapping from a low-dimensional feature space to a high-dimensional space that captures the underlying neural process of speech production, and thus is a first-of-its-kind speech feature representation to be used in assessing speech disorders. This novel feature representation, with the possibility of additional features extracted from the initial novel feature representation (e.g., the coordination characteristics of these features), provides the basis for a unique set of classifiers of condition state and predictors of condition severity.

Throughout the following description, parameters of the model may be referred to as control parameters. However, control parameter is an umbrella term for all numerical values (single values or timeseries) that are input to the system, derived through intermediate processing steps, and output from the system. For example, control parameters of the speech control model include but are not limited to articulatory trajectories, neural muscle activations, acoustic signals, neural synaptic weights, model delays, model gains, and neural firing rates throughout the speech production-speech perception control loop. Furthermore, we use the term "speech-related" signal as an umbrella term for all biological signals related to speech. Speech-related signals include but are not limited to the acoustic speech waveform, non-acoustic signals such as accelerometer measures of the vocal source, facial expressions during speech production, neural activity during speech production such as that measured by magnetic resonance imaging, electroencephalography, magnetoencephalography, or positron emission tomography, articulator positions such as those measured by electroarticulography, electromyography of the body, and respiratory measurements.

To date, we have applied this approach using features derived from (neural) feedforward articulatory commands and auxiliary source variables, but it is also applicable to neural features derived from auditory and somatosensory feedback errors. Also, to date the approach has been applied to prediction of the severity of Parkinson's disease and major depressive disorder, but it is applicable to any condition that can be modeled with neural computational structures. Examples include traumatic brain injury (TBI), Amyotrophic lateral sclerosis (ALS), often referred to as Lou Gehrig's Disease, Multiple Sclerosis (MS), and dementia, as well as effects due to physical and cognitive stress and sleep disorders, all of which show voice aberrations. Tele-monitoring of treatment for such conditions and detection of early stages in the disease are also an important application area. In addition to the broad sensitivity of neurocomputational model based features, these features may offer greater specificity and consequently allow discrimination between different neurological disorders using an inferred brain basis.

Figure 2:
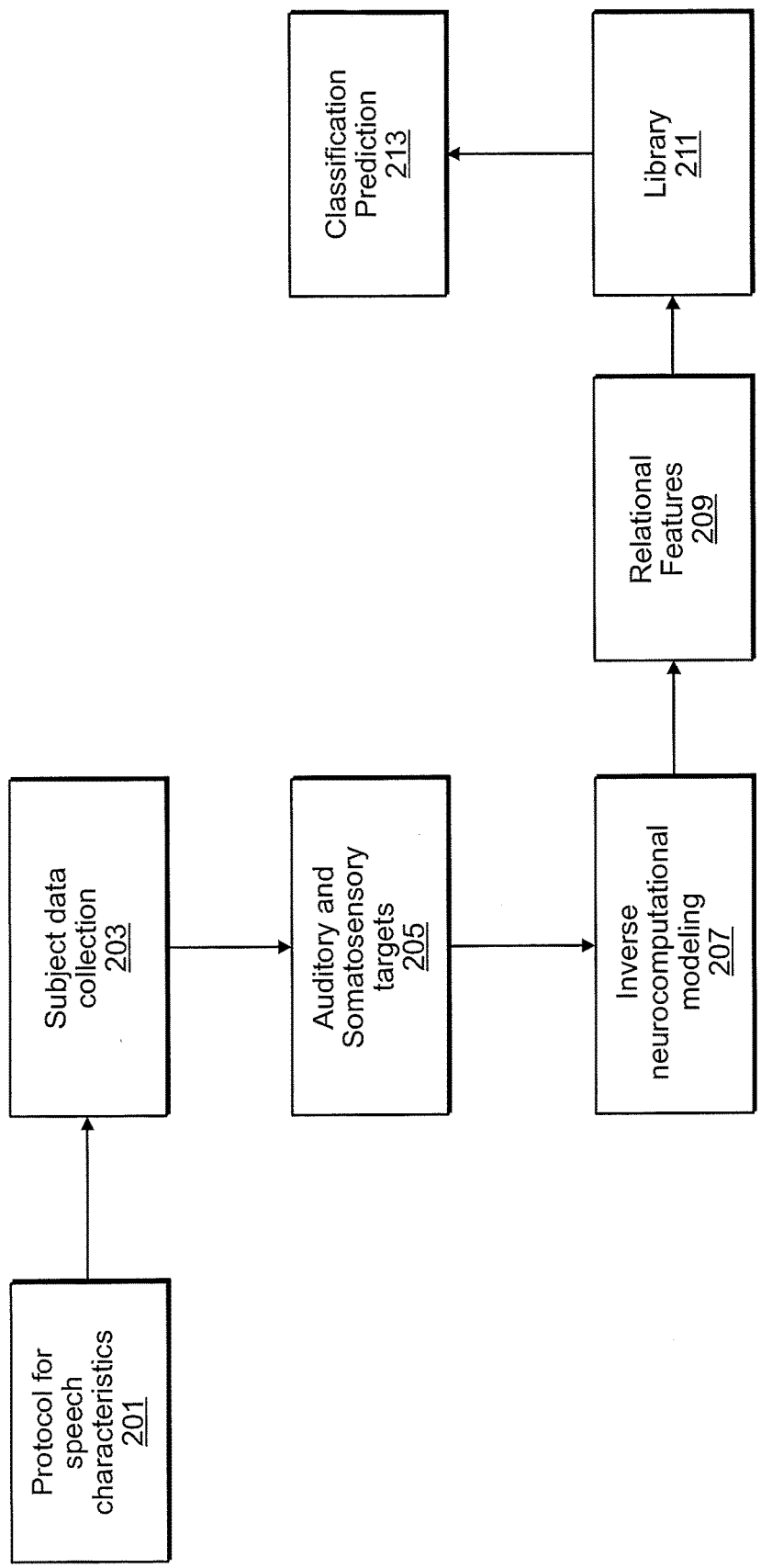
FIG. 2 is a block diagram of an embodiment of the invention.

One embodiment of the present invention is illustrated in FIG. 2. To collect speech-related data, a protocol is established at 201. The protocol is tuned to cognitive and motor articulatory and laryngeal declines of interest. It may be based on free speech or any one of many known protocols including reading passages such as the Rainbow passage [29], the Caterpillar passage [28], the Grandfather passage [30, 31] or the North Wind [32] passage. Using the protocol, data is collected at 203 from many subjects including those with disorders of interest. Example disorders include Parkinson's disease, depression, ALS, TBI, Alzheimer's, autism and schizophrenia. From the collected data, features of the speech are extracted and used as auditory targets. For example, to use the standard DIVA model, three formant frequencies and the fundamental frequency are extracted. In an alternative, using a vocal source model, fundamental frequency only is extracted. Many other speech features for comparison, such as phoneme-based durations, vocal source aspiration, voice/unvoiced states, and respiratory modulation, can also be used as DIVA targets. The extracted data is applied to a neurophysiological computational model that performs an inverse operation to go from speech features to internal model parameters 207. The model may, for example, be DIVA model. Data developed in the model 207 results in a higher dimensional representation than the data directly extracted from the speech. That data may be converted to yet higher dimensions through a relational features process 209 which may, for example, be based on correlation or coherence or other statistical or deterministic transformations. Either the data directly from the neurophysiological computational model or the relational features output, or both together are stored in a library 211 using any of the various pattern matching models such as the Gaussian Mixture Model (GMM), Support Vector Machines (SVM) or Deep Neural Network (DNN) at 211 [33].

In subsequent use of the system to analyze a specific individual, data is collected at 203 using the same protocol 201 to extract the target data at 205 to be applied to the neural computational model 207. The data derived from that model is similarly converted at 209 if the library at 211 is based on such converted data. The data of the test individual is then compared to the stored data for individuals of known disorders according to the appropriate model at 211 to obtain a prediction of a disorder for the individual at 213. The output from 213 may include a probability that the individual suffers the disorder and/or a prediction of the severity of the disorder.

To add technical detail to FIG. 2, we can elaborate on the full process and the individual functional steps. The method for estimation of neurological disorders from vocal biomarkers begins with collection of speech data from subjects. We can describe the latent neurological state by a categorical or real valued random variable Z. If Z is categorical, then Z represents one of many possible disorders and would be used for classification (e.g, Parkinson's disease vs ALS vs depression). If Z is real valued, it may represent the severity of a disorder. In depression, Z could correspond to the depression severity from a self report form or a clinician assessment. The neurophysiology of the individual can abstractly be represented by a function, $\Theta=f(Z)$, that transforms the neurological disorder of the person into a series of unobserved neurophysiological states that encompass all of the model parameters of the person $\Theta$. The neurophysiological states give rise to observable speech-related signals, X, which include vocal biomarkers that can be measured through microphones in a clinical, home, or mobile application setting. This transformation is represented as $X=G(\Theta)$. The ultimate goal of any estimation method is to determine Z using X. A key step in our approach is to infer and leverage the intermediate values $\Theta$ to estimate Z.

The nonlinearity of the control model and critically the neurophysiologically constrained space result in additional information about the subject in $\Theta$ than can be obtained with the speech related features alone. Specifically, we are using known neurobiophysical mechanisms to constrain the composite mapping function $X=G(f(Z))$, and we explicitly leverage the latent parameters $\Theta$. The latent parameters are estimated through an inversion process. Further detail on the inverse neurocomputational model box is deferred to the following section, so we continue with the system diagram.

For every subject, we estimate the latent parameters from their observed vocal waveform. We then collect these subject-specific parameters in a library of patterns $\Theta_k \sim L(Z)$, where $\Theta_k$ is a subject-specific parameter set added to the library L(Z). We also create additional patterns, $\gamma_k$, where $\gamma_k = H(\Theta_k)$ and H represents additional processing functions 209 such as correlation analysis, or summary statistics such as minimum, maximum, mean, median, mode, standard deviation, and range. As part of building the library 211, we know subjects are associated with a particular disorder, Z or have a severity measure. The full set of patterns $(\Theta_k, \gamma_k, z)$ for all k subjects and z disorders are processed in a final step by a machine learning algorithm or ensemble of algorithms, M. M may be a Gaussian mixture model, a deep neural network, a support vector machine [33], or a random forest to name a few examples. Using the training data, which consists of tuples $(\Theta_k, \gamma_k, z)$, M learns a relationship between the features $(\Theta_k, \gamma_k, z)$ and the disorder. The process of learning the relationship between features and disorders is called training. Using the learned relationship from the training data, M takes a tuple of $(\Theta_i, \gamma_i)$ for subject i, with unknown neurophysiology z, and predicts the disorder, $\hat{z}$. We distinguish z from $\hat{z}$ by noting z as the true disorder and $\hat{z}$ as the estimate. The process of predicting an unknown disorder from features is called testing.

When a new subject with unknown pathology is presented to the system, the algorithm estimates the latent parameters, $\Theta_i$, and performs processing to create additional patterns, $\gamma_i$. As stated previously, the tuple $(\Theta_i, \gamma_i)$ is then processed by the machine learning algorithm M to return an estimate of the neurological disorder or disorder severity z. In both the training and testing phase, the feature tuple $(\theta, \gamma)$ may contain either $\theta$ or $\gamma$ or both values.

In our invention, we take advantage of a neurologically plausible, fMRI-validated computational model of speech production, the Directions into Velocities of Articulators (DIVA) model [13], though our approach is compatible with sensorimotor neurological modeling more generally. The DIVA model takes as inputs speech formants (vocal tract resonances) [1][2] and the fundamental frequency (pitch) of a speech utterance. Then, through an iterative learning process, the model computes a set of parameters that correspond to different aspects of the speech production process including articulatory commands and auditory and somatosensory feedback errors. We hypothesize that with a neurological, traumatic, or cognitive-stress condition, speech changes from impairments along the speech production (or modulating) pathway. Therefore, when the model is trained on speech from a condition, the internal variables will reflect the type and/or severity of the disorder. More generally, sensorimotor disorders will be reflected in changes to neural organizational principles of this type [10][11]. Using these internal "brain state" variables may offer greater specificity than non-neurocomputationally based features that do not attempt to model the underlying neuropathophysiology.

Figure 3:
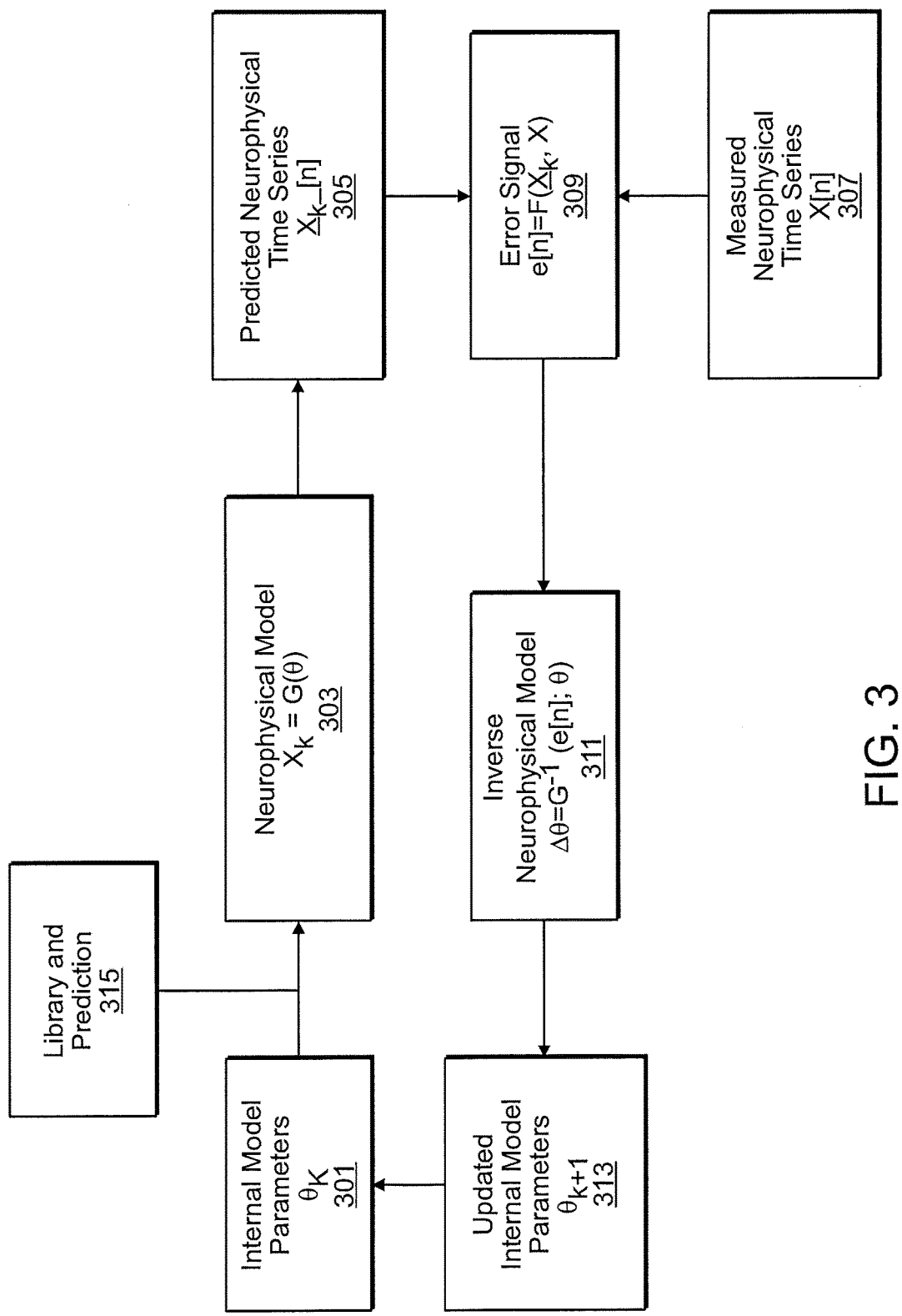
FIG. 3 is an illustration of the inverse neural computational modeling and library of FIG. 2 in one embodiment of the invention.

The mathematical framework of one embodiment is in FIG. 3. In our frame work, a neurophysiological model is parameterized by a set of control variables 301 represented as Θ. These parameters are input to the neurophysiological computational model 303 which generates a predicted time series 305. The predicted time series is compared against measured values 307 from the subject, and the difference 309 is used in an inverse model 311 to update the model's estimates of the internal parameters 313.

The algorithm is as follows:
1. Initialization: Initialize model parameters Θ
2. Model Loop:
    2a. Create a predicted multidimensional time series, indexed by time sample or iteration k, given model parameters,
    2b. Compute error between predicted time series and measured time series, $e[n]=F(X_k, X)$
    2c. Map error into model parameter correction $\Delta\Theta_k = G^{-1}(e[n]; \Theta)$ 2d. Update model parameters, $\Theta_{k+1} = \Theta_k + \Delta\Theta_k$ 2e. Exit loop after N iterations or error criteria being reached
3. Optionally perform additional feature extraction in model parameter space (correlation analysis, coherence, multivariate regression), In a conventional system, speech features would be extracted directly from the measured data 307 for subjects of known disorder to collect data for a prediction library. Then, like data would be extracted for an individual being assessed and that data would be compared to the library. By contrast, here the extracted data is applied through a loop including the inverse model 311 and forward model 303 to develop model control parameters data over multiple iterations of the loop. It is those control parameters, or data converted from those control parameters, that are then stored in a library. When an individual is tested for a disorder, the individual's speech-related data is cycled through this process to develop parameters for that individual that can be compared to the stored data in the library.

Figure 4:
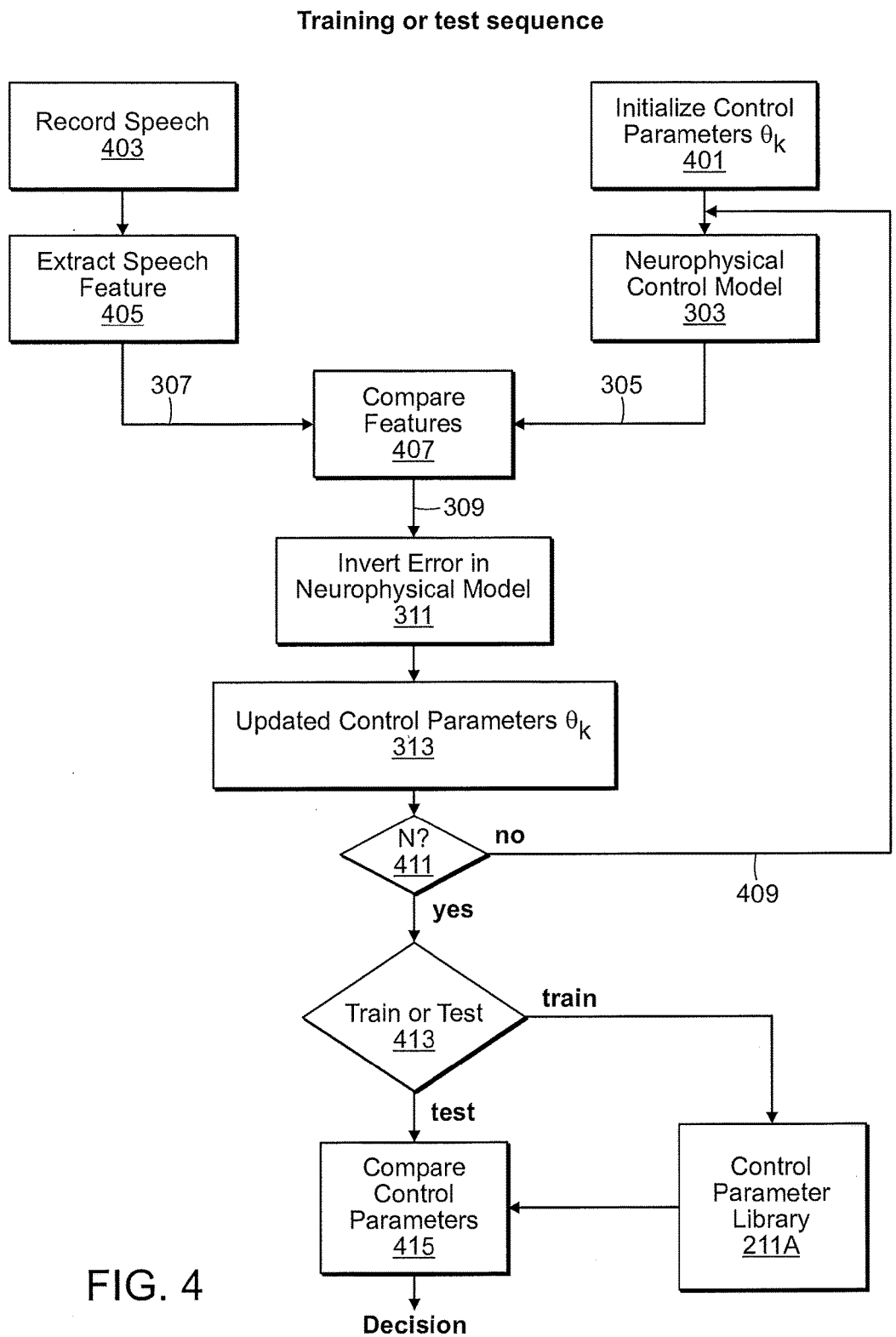
FIG. 4 is a flowchart illustrating operation of one embodiment of the invention using the system of FIGS. 2 and 3.
Figure 5:
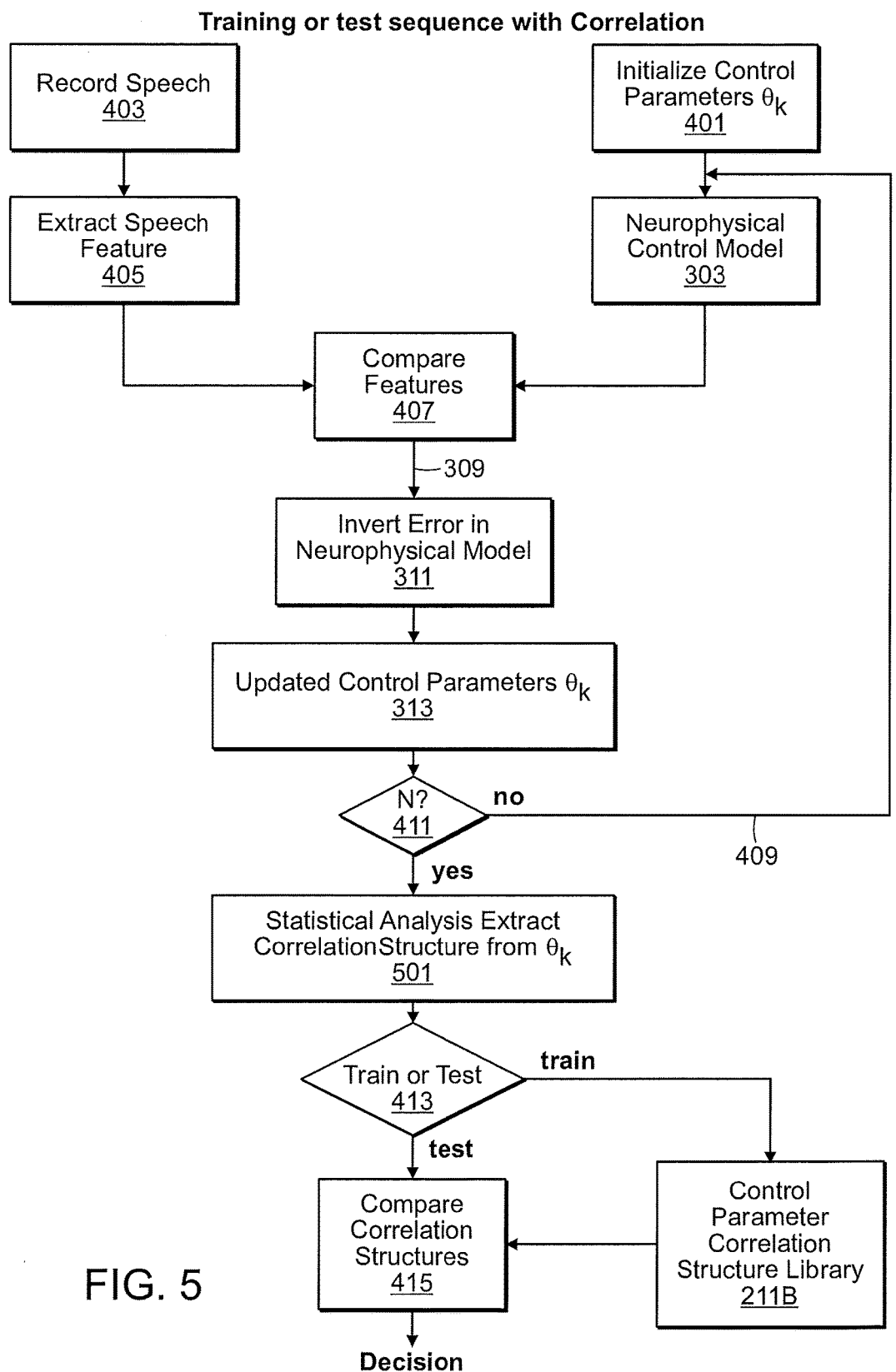
FIG. 5 is an alternative flowchart similar to FIG. 4 additionally including a statistical analysis of the updated control parameters.

Flowcharts for processing of the data in the system of FIG. 3 are presented in FIG. 4 and, for the case of additional statistical analysis on the control parameters, in FIG. 5. The neurophysiological control model 303 is first initialized by target control parameters θ 401. Speech is recorded, for example at a clinical, home or mobile source, at 403 and speech features used in the testing are extracted at 405. A recorded speech may be from subjects of known disorder in order to generate data to be stored in the library, or it may be from a test subject to be analyzed based on the stored data.

At 407, the extracted speech features from the individual are compared to that generated in the neurophysiological control model at 407 to generate the error signal 309. The error is then inverted in the neurophysiological model 311 to update the control parameters at 313. If the system has not yet cycled through a required number of iterations, or met a minimum error criteria, it returns to apply the updated control parameters to the neurophysical control model through the loop 409. Once the control parameters have stabilized to the appropriate degree at 411, the system proceeds to 413. From here, during a training mode, the updated control parameters are stored with the known disorder in the control parameter library. On the other hand, during a test sequence for an individual, the updated control parameters for the individual are compared to those in the library 211 at 415 using the appropriate pattern matching model.

In the case where additional analysis is to be applied to the updated control parameters for feature extraction prior to library collection or comparison, the process is as illustrated in FIG. 5. The process is substantially the same as that in FIG. 4 except that an additional analysis, for example to extract correlation structure from the updated control parameters, is provided at 501. The library to 211B then stores that correlation structure data and likely also the original control parameters along with the disorder.

In one embodiment, the correlation structure features are derived from the DIVA model's 13 time-varying (feedforward) position states, which are sampled at 200 Hz. The input in this embodiment is 3 formant frequencies and the fundamental frequency. The formant tracks were extracted using a Kalman Autoregressive Moving Average software [2] and the fundamental frequency with Praat [17].

In both training and testing, the model parameters that get updated are initialized to "neutral" configurations with respect to the model. For DIVA, the vocal tract parameters (1-10 of the 13 dimensional space) are set to a neutral/open configuration of zero. Dimensions 11, 12, and 13 are the fundamental frequency, source air pressure, and voicing indicator. Fundamental frequency is initialized to 0.0, source air pressure is set to −0.5, and voicing is initialized to 0.0. Software for the DIVA component was downloaded from [25] and modified to fit in FIG. 4.

The DIVA auditory targets are zones centered around the true target. The error signal is modulated depending on whether and how far the sensed production falls outside the auditory target zone. The fundamental frequency and formants are set to 90% and 110% of the participant specific extracted values. Praat parameters included a 1 ms time step, the autocorrelation method of fundamental frequency determination, and a minimum and maximum range of 75 and 600 Hz. If a fundamental frequency was not detected, the minimum and maximum ranges were set to 1 Hz and 1000 Hz respectively.

For DIVA, the somatosensory targets are also specified in terms of zones. The minimum and maximum placement of articulators for six of the eight somatosensory signals are initialized to −1 and −0.25. The somatosensory targets for pressure and voicing minimum and maximum are initialized to 0.75 and 1.0.

This process represents a 3-to-13 expansion to a higher-level neural space. Articulatory states comprise positions and velocities of articulators such as of the tongue, jaw, lips, and larynx. We performed 10 model iterations and output the 13 articulatory features at the conclusion of the 10 iterations. These features were further processed using an advanced form of intra and interfeature correlation analysis, but they can be processed by any desired machine learning framework to extract "features of features" [16].

Figure 6:
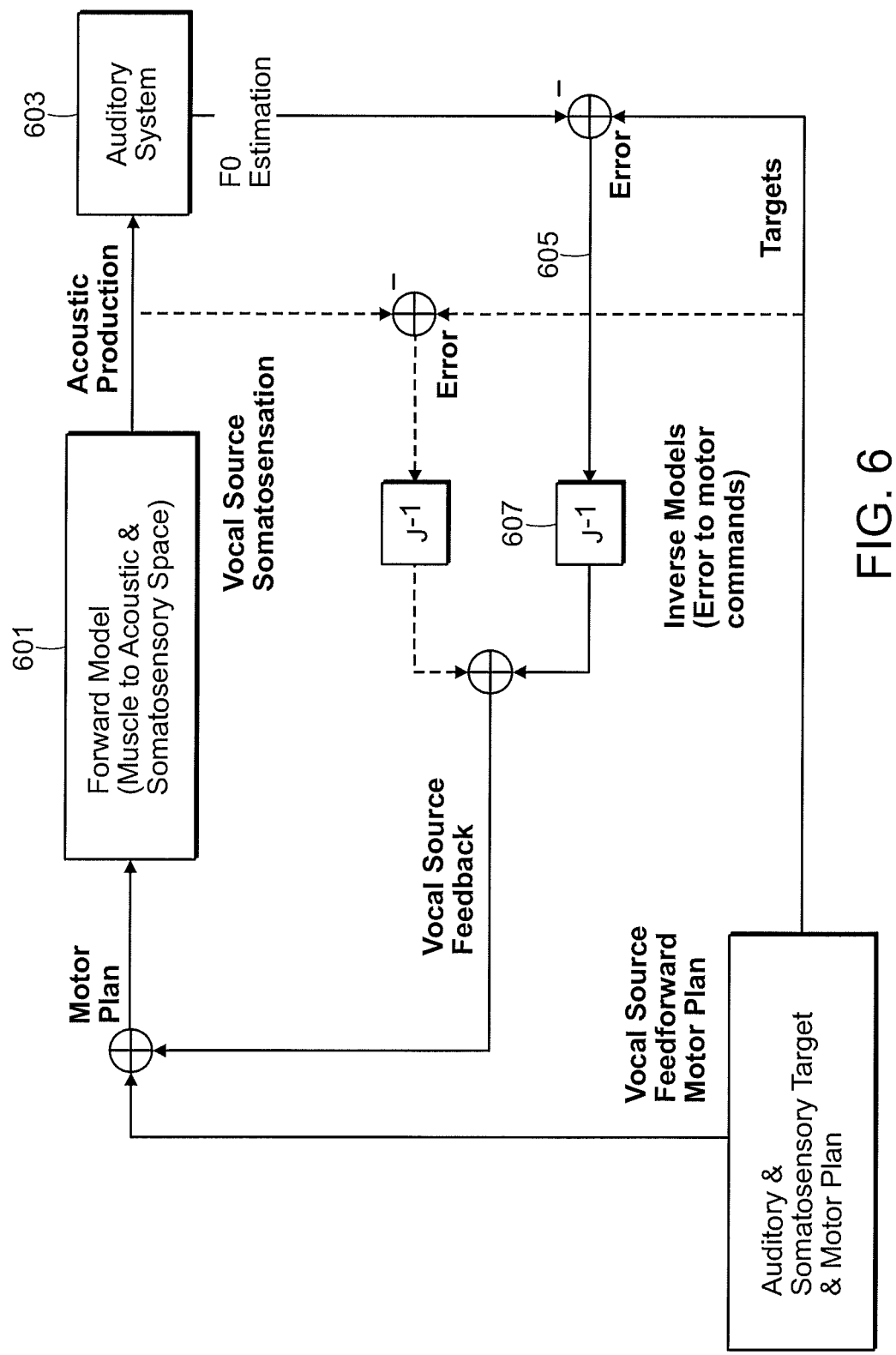
FIG. 6 is an illustration of an alternative to the DIVA model for use in an alternative embodiment of the invention.
Figure 7:
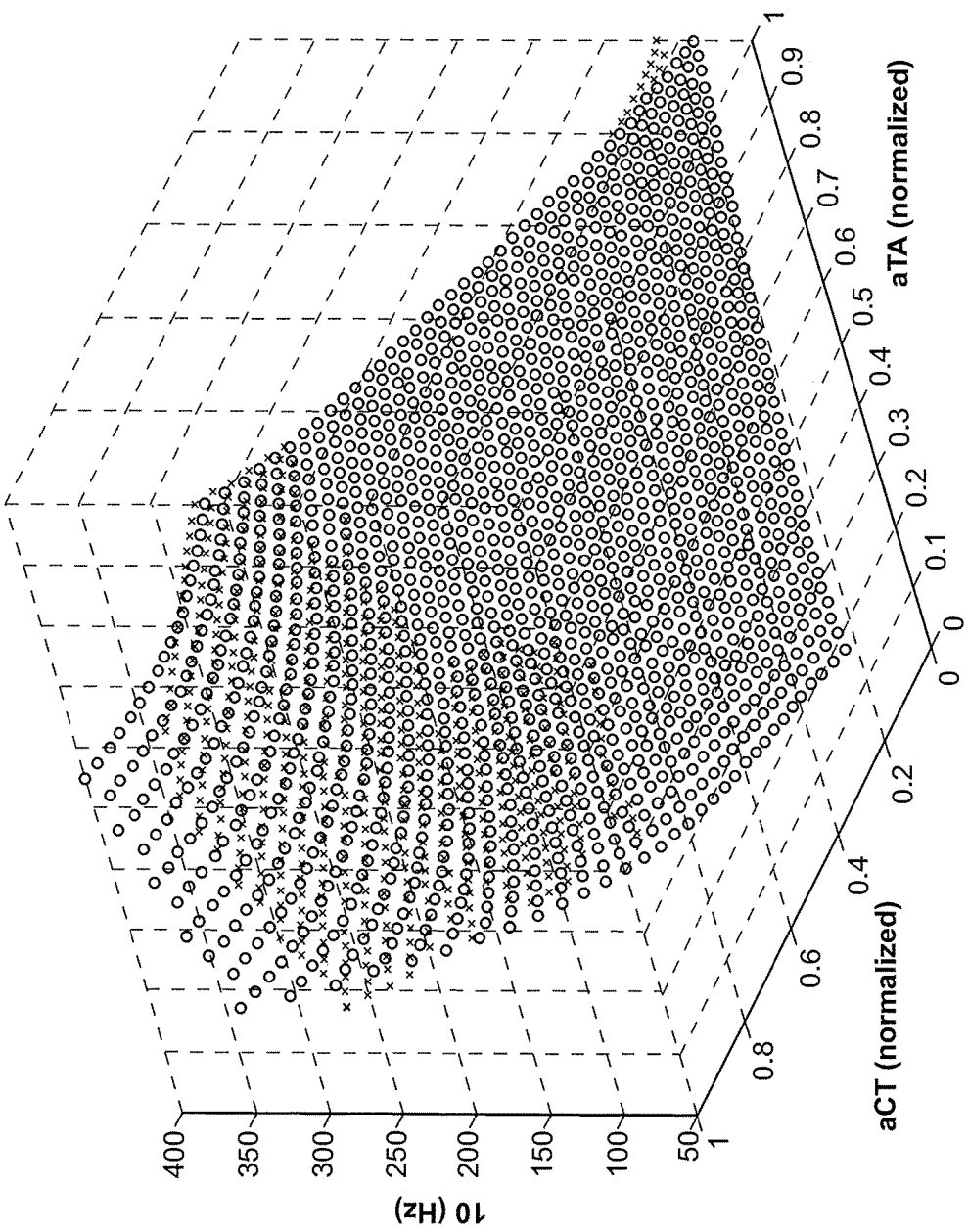
FIG. 7 is a numerical visualization of the mapping function of the forward model of FIG. 6.

In another embodiment of the invention [27], we created an entirely new software instantiation of the process in FIG. 2 using the model of FIGS. 6 and 7 in order to have a neural model of the vocal source. The overall system diagram is similar to [22] in that both systems are modeling feedforward and feedback control of the vocal source, but critically different in that our system performs a sensorimotor transformation step and uses a neurobiophysical component as part of the sensorimotor transformation.

The embodiment of this invention follows the block and flow diagrams in FIGS. 2-5, but we provide specific engineering details. Our procedure for estimating neural signals that control the vocal source, followed by further processing in order to assess neurological disorder severity follows the essential principles of the invention. Those skilled in the art will recognize that the specific embodiment we discuss need not limit the invention to the vocal source.

Specifically, the vocal source controls a person's fundamental frequency, perceived as pitch, through the interaction of several muscles. Two key muscles in the modulation process are the cricothyroid and thyroarytenoid muscles. These two muscles are controlled by the brain through branches of the tenth cranial nerve, the vagus nerve. For the sake of brevity, we will refer to the neural control of the thyroarytenoid muscle as aTH and the neural control signal of the cricothyroid muscle as aCT. The objective of the full neurophysical computational model will be to estimate these unobserved neural control signals using a speech sample.

In this alternative embodiment, the model in FIG. 6 is used in the diagrams of FIGS. 3-5. Here, the forward model is of control of the vocal source exclusively and in high detail as opposed to an emphasis on the vocal tract in FIG. 1. The mapping function of the forward model 601 can be seen in the numerical visualization of FIG. 7. The visualization is of the true neurobiophysical mapping function (circles) and quadratic approximation (X's). Truth values were obtained from fundamental frequency estimates of the glottal waveform, and approximation values were generated from the second order polynomial fit with ordinary least squares to the true data. The glottal waveform was simulated offline for a canonical speaker in order to create the truth data for the mapping function.

In this embodiment, the forward model 601 drives the auditory system (implemented as an identity function) 603 to provide a fundamental frequency which is compared to the subject's fundamental frequency to generate an error 605. The error 605 is applied through an inverse model 607 to create the feedback based update to the control parameters. The feedforward and feedback gains are omitted for clarity. In this embodiment, the control parameters are the muscle control signals aTH and aCT. Unlike the conventional DIVA model, the somatosensory feedback was not considered necessary, but could be added in future realizations.

A key, novel component of this embodiment is a biophysically inspired model of the two major muscles and the activations associated with them in the vocal source. We need to establish a mathematical relationship between the neural activation signals and the fundamental frequency. We develop this relationship by building upon a prior biophysical model of the vocal source [18-20]. In particular, we quantify the relationship between the two muscle activations and the vocal source by fitting a second order, two-dimensional polynomial with cross terms to data generated from a model of the vocal source.

The model of the vocal source is an ordinary differential equation of a canonical larynx. Two input parameters to the model are muscles activations. However, the output of the model is a glottal waveform (the puffs of air that exit the vocal folds before being shaped into speech by the vocal tract). The frequency of the puffs of air is the fundamental frequency of the ultimately produced speech waveform. We create a table of neural input strengths for each of the two muscle activations, from least activated, to most activated, and compute the glottal waveform for each muscle activation tuple. A muscle activation tuple is the joint specification of aCT and aTH, written as (aCT, aTH). For each glottal waveform, we use a threshold-based peak detection algorithm to identify the periodic puffs of air. We compute the difference in time between each air puff in order to estimate the fundamental frequency for the tuple. We take the median estimated fundamental frequency to be robust to errors in peak detection. This procedure is repeated for each tuple in our list of muscle activations.

With a complete list of muscle activations and corresponding fundamental frequency, we use ordinary least squares to fit a paraboloid of the form $z=Ax^2+Bxy+Cy^2+Dx+Ey+F$, where A, B, C, D, E, F are constant coefficients estimated from our list of tuples. The aCT and aTH values are x and y, and z is the fundamental frequency. Thus we have established a functional relationship between aCT, aTH, and fundamental frequency.

To estimate aCT, and aTH values, which are unknown for a person's spoken speech, we need to estimate the fundamental frequency for the speech, and we must iterate through the process diagrammed in FIG. 3-5. The extraction of fundamental frequency is accomplished using the freely available Praat software, but those skilled in the art will recognize that any fundamental frequency estimation algorithm could substitute equally well.

As an additional step, we normalize each person's fundamental frequency trajectory by adding or subtracting an offset, if necessary. This normalization step changes the absolute value of the person's fundamental frequency trajectory, and it is only applied under certain conditions. The step places the person's fundamental frequency within the fundamental frequency bounds that would be appropriate for our derived functional relationship between muscle activation and fundamental frequency. We also excise non-voice regions of speech and concatenate the remaining voiced pieces (ie., we only analyze the portions of the speech waveform that have a non-zero fundamental frequency). Unvoiced speech is not analyzed but can be included in expanded speech feature and auditory and somatosensory target sets.

To advance through the model described in FIG. 3-5, we begin by initializing the model's two muscle activations to a medium level of activation. Through iterative refinement, we will improve our estimate of the unobserved muscle activations as follows.

First, we initialize the auditory target of the brain to the observed, normalized fundamental frequency we have extracted from the speech waveform. Then, we use the current level of muscle activations and our functional relationship to generate the corresponding fundamental frequency f0 at the first instant of time in the speech waveform. After that, we compare the generated f0 value to the auditory target f0 value for the corresponding instant of time. The comparison is done with a difference operation, but more sophisticated error generation mechanisms could be used, such as a nonlinear transformation applied to the difference operation. The error signal, in conjunction with an estimate of the muscle activations that were used to generate the f0 value, are used to create a muscle update command. We call the creation of the muscle update command from the error signal the sensorimotor inversion process.

The mathematical operation that implements the sensorimotor inversion makes use of the pseudoinverse of the Jacobian of the functional relationship between the muscle activations and the fundamental frequency. We establish the Jacobian by taking the matrix of partial derivatives associated with the functional relationship. Because the matrix is not square, no inverse exists. Therefore, we use the Moore- Penrose pseudoinverse to create a pseudoinverse of the Jacobian. The multiplication of the pseudoinverse by the error signal results in an update command.

The motor feedback command is delayed by a suitable portion of time to represent the neurophysiological auditory delay in humans. Additionally, the motor update command is scaled by a feedback gain factor before being added to the current feedforward motor gain. The delay, $n_d$, is introduced by computing an error update at time, n, using the produced signal, $y[n-n_d]$ as opposed to $y[n]$. The feedforward, $\alpha_{ff}$ and feedback $\alpha_{fb}$ gains weight the feedforward, $x_{ff}[n]$ and feedback $x_{fb}[n]$ motor commands to create the composite command, $x[n]:x[n]=\alpha_{ff}x_{ff}[n]+\alpha_{fb}x_{fb}[n]$. The gains are always both positive, sum to one, and are chosen empirically for system performance. The gains and delays are kept constant for all subjects but, like the aCT and aTH values, could also be learned in other embodiments. The new, composite motor plan is then used to generate a new fundamental frequency value. The new fundamental frequency value is compared to the auditory target for the timestep, an error signal is generated, the sensorimotor transformation takes place, and a new motor feedback update is generated. This process continues for each time sample in the fundamental frequency target derived from a person's speech. When the last sample is generated, all of the motor updates from the error signals are used to modify the feedforward neural plan in the model's brain. The updated feedforward neural plan is then used, and the whole process is repeated. Thus by iterating both within and across time, gradually, the auditory signal generated using the iteratively updated neural plan will converge or the iterative process will be stopped after a fixed number of iterations. Upon conclusion, the estimated neural aCT and aTH values are taken from the model and used in the next phase of the process.

In the latent space discovered by the model, the two time series inferred, the aCT and aTH neural activations, are used in a further estimation step to extract additional patterns for the subject under evaluation. Each of these time series individually may contain information that is representative of a neurological disorder. However, we take the additional step in our algorithm by analyzing the interaction between the time series. Thus, another novel aspect of this invention is the recognition that the coordination between the time series is crucial for estimating informative features. No prior work has used the coordination between neural signals as a defining contribution to their methodology. Though we used the coordination in this specific embodiment, other relations within and between the time series may also be informative and provide complimentary information.

Specifically, we process the two time series using the cross correlation procedure first proposed by Williamson et al [16]. Briefly, we compute the autocorrelation of each time series and their cross correlation to create four new sequences of data. Each time correlation sequence is subsampled at different delay scales in order to fill a block matrix. The eigenvalues of the matrix are computed and used as features. The application of the Williamson et al [16] correlation code to the muscle activation timeseries is a unique step in the process, and it completes the procedure for estimating patterns that may be indicative of a neurological disorder.

Pattern estimation per person is one step of the process. The full system requires estimating these patterns for many subjects who are known to have a disorder to create a library of patterns. Then, a new subject with an unknown disorder is analyzed to create their pattern. The new subject's pattern is compared against the library of patterns using the machine learning technique Extremely Randomized Trees. Other machine learning techniques such as support vector machines or Gaussian Mixture Models [33] are alternative or even complimentary algorithms to the Extremely Randomized Tree algorithm [21].

Although our description above is specific to speech and Parkinson's disease and major depressive disorder (the two application areas thus far addressed), the key contribution is that modeling the system parameters (or "state space") provides a novel way of defining features. The forward computational model is not only a model of the neurological underpinnings of motor behavior but also of the interactions of the neural substrate with physical articulators. Due to physical constraints, the speech articulators and (other) components of the speech system can jointly occupy only a small fraction of the articulator state space, and the effect of neural damage on articulator trajectories or of damage to the articulators themselves on those trajectories could be captured in a model, and therefore could provide useful features. The general space covers vocal, biomechanical, kinematic, and dynamic models of all aspects of speech at multiple time scales from phones to sentences. We are explicitly including the idea that our forward model (for example, DIVA) employs the physical constraints governing joint articulator movements (and others, such as laryngeal and respiratory muscles), so this provides benefit when the inverse mapping from measurement space (for example, audio features) back into the model state space is performed. The general concept for this application is that modeling the control parameters of a physical system rather than just the output will provide greater benefit (i.e. lower error).

Advantages Over Existing Methods

Although there has been significant effort in using potential vocal (and other sensorimotor) biomarkers for neurological disorder, stress, and emotion classification, there has been no exploitation of biomarkers that result from inverse engineering neural models of the condition. Many systems focus on data centric, acoustic features such as jitter, shimmer and mel frequency cepstral coefficients. These features are then combined in a regression or classification framework such as an artificial neural network or Gaussian Mixture Model for affect estimation or disorder severity prediction [3]. By contrast, a branch of computational psychiatry specifically seeks to use observed patient features in order to fit a neurobiologically inspired representation of the disorder that encapsulates an explanation of the observed symptoms [12]. Our model is related in direct fashion to known neurobiological function, and relationships that are localized in the brain, larynx, and vocal tract. This neurobiological focus on the speech system distinguishes our approach from [12] which emphasizes psychological process models that describe response inhibition or decision making for example. Consequently, our parameter estimates for severity may point more directly to causes of dysfunction and possible points of treatment than traditional approaches. Prior work [14,15] has demonstrated that inferring articulatory parameters from acoustic data improved speech recognition error rates. However, in [15] this inference was not based on a neurophysical computational model, but from known mappings between the biomechanics and acoustics. It used an implicit model of articulator position to acoustic output. The known mappings are coarse approximations such as vowel height, and tongue front-back position. By contrast, the DIVA mappings (and other speech related sensorimotor mappings) may have significant specificity, and allow building a model to match a specific speaker instead of a generic speaker, while also allowing specificity across disorders. In our case, individualization occurs because we are reproducing a given speaker's formant trajectories and other speech features for an utterance rather than one generic set of formant tracks for the utterance. Other forms of individualization could incorporate additional information about their medical history or demographics (age, gender, height, weight), structural information derived from Mill scans of the brain, articulators, and larynx, and current or past medication consumption, and smoking history.

The advantages of the neurophysical computational model over a purely biomechanical model such as [23, 24] are three fold. First, the neurophysical model provides a holistic description of the speech motor system and its dynamics. Consequently, it affords multiple points of insight into the underlying neurophysiology. Second, the inversion process that is part of the neurophysiological model takes place in a neurobiologically plausible manner. Consequently, the estimated patterns of activity may be more accurate and less prone to artifacts than methods that take a purely statistical approach to parameter estimation. Third, the neurophysiological model provides a direct avenue for assessment of neurobiological structures that are known to be directly involved in different disorders. For example, Parkinson's disease is characterized by degradation of the substantia nigra pars compacta, a specific region of neural tissue deep in the brain. In a biophysical model that is limited to only considering the movement of the laryngeal muscles or the speech articulators, patterns that are estimated from these components of speech system may be noisy or non-specific. By estimating level of activity in key brain areas through the effect of these areas on the core speech network and in turn on the laryngeal muscles and articulators, a neurophysiological model can be both more sensitive to the presence of a disorder and more discriminating between different disorders as different disorders may have differential effects on neuronal regions.

Commercial Applications

There is growing interest in the use of vocal biomarkers for detecting changes in mental condition and emotional state, which reflect underlying changes in neurophysiology. Example conditions include Major Depressive Disorder (MDD), Parkinson's, and speech, language, and articulation disorders. Other applications in which neuro-motor and neurophysiological coordination can break down include early onset detection of traumatic brain injury (TBI), Amyotrophic lateral sclerosis (ALS), often referred to as Lou Gehrig's Disease, dementia (including Alzheimer's disease) and Multiple Sclerosis (MS), as well as effects due to physical and cognitive stress and sleep disorders, all of which show voice (and other sensorimotor) aberrations in early stages. Tele-monitoring of treatment with all such conditions is also an important application area.

The automated system of the present application may be just hardware, but is generally implemented in software in a hardware system comprising a data processor, associated memory and input output devices (e.g., keyboard, mouse, displays, printers, microphone, speakers, etc.). The processor routines and data may be stored on a non-transitory computer readable medium as a computer program product. The system may, for example, be a standalone computer, a network of devices, a mobile device or combination thereof.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

REFERENCES

[1] D. Rudoy, D. N. Spendley, and P. Wolfe. Conditionally linear Gaussian models for estimating vocal tract resonances, *Proc. Interspeech*, 526-529, 2007.

[2] D. Mehta, D. Rudoy, and P. Wolfe Kalman-based autoregressive moving average modeling and inference for formant and antiformant tracking. *The Journal of the Acoustical Society of America*, 132(3), 1732-1746, 2012.

[3] J. R. Williamson, T. F. Quatieri, B. S. Helfer, R. Horwitz, B. Yu, D. D. Mehta. Vocal biomarkers of depression based on motor incoordination. *AVEC* 2013.

[4] J. Mundt, P. Snyder, M. S. Cannizaro, K. Chappie, and D. S. Geraits. Voice acoustic measures of depression severity and treatment response collected via interactive voice response (IVR) technology. *J. Neurolinguistics*, 20(1): 50-64, 2007.D.

[5] T. F. Quatieri and N. Malyska. Vocal-Source Biomarkers for Depression: A Link to Psychomotor Activity. *Interspeech*, 2012.

[6] A. Trevino, T. F. Quatieri, and N. Malyska., Phonologically-Based Biomarkers for Major Depressive Disorder. *EURASIP Journal on Advances in Signal Processing: Special Issue on Emotion and Mental State Recognition from Speech*, 2011(1), 1-18, 2011.

[7] D. Sturim, P. Torres-Carrasquillo, T. F. Quatieri, N. Malyska, and A. McCree. Automatic Detection of Depression in Speech using Gaussian Mixture Modeling with Factor Analysis. *Interspeech*, 2011.

[8] B. S. Helfer, T. F. Quatieri, J. R. Williamson, D. D. Mehta, R. Horwitz, and B. Yu. Classification of depression state based on articulatory precision. *Interspeech*, 2013.

[9] Asgari, Meysam, Izhak Shafran, and Lisa B. Sheeber. "Inferring clinical depression from speech and spoken utterances." *Machine Learning for Signal Processing (MLSP), 2014 IEEE International Workshop on. IEEE*, 2014.

[10] E. Tognoli and J. A. Scott Kelso. Brain coordination dynamics: True and false faces of phase synchrony and metastability. *Prog Neurobiol*. 87(1): 31-40, 2009.

[11] S. L. Bressler, E. Tognoli, Operational principles of neurocognitive networks. *International Journal of Psychophysiology* 60:139-148, 2006.

[12] Wiecki, Thomas V., Jeffrey Poland, and Michael J. Frank. "Model-Based Cognitive Neuroscience Approaches to Computational Psychiatry Clustering and Classification" *Clinical Psychological Science* 3.3 (2015): 378-399.

[13] Tourville, Jason A, and Frank H Guenther. "The DIVA model: A neural theory of speech acquisition and production." *Language and Cognitive Processes* 26.7 (2011): 952-981.

[14] King, Simon, et al. "Speech production knowledge in automatic speech recognition." *The Journal of the Acoustical Society of America* 121.2 (2007): 723-742.

[15] Livescu, Karen Feature-based pronunciation modeling for automatic speech recognition. Diss. Massachusetts Institute of Technology, 2005.

[16] Williamson, J. R., Bliss, D., Browne, D. W., and Narayanan, J. T., Seizure prediction using EEG spatiotemporal correlation structure. Epilepsy Behav., vol. 25, no. 2, pp. 230-238, 2012.
[17] Boersma, Paul & Weenink, David (2015). Praat: doing phonetics by computer [Computer program]. http://www.praat.org/
[18] I. R. Titze and B. H. Story, "Rules for controlling low-dimensional vocal fold models with muscle activation," The Journal of the Acoustical Society of America, vol. 112, no. 3, pp. 1064-1076, 2002.
[19] B. H. Story and I. R. Titze, "Voice simulation with a body-cover model of the vocal folds," The Journal of the Acoustical Society of America, vol. 97, no. 2, pp. 1249-1260, 1995.
[20] M. Zañartu Salas "Influence of acoustic loading on the flow induced oscillations of single mass models of the human larynx," Ph.D. dissertation, Purdue University West Lafayette, 2006
[21] P. Geurts, D. Ernst, and L. Wehenkel, "Extremely randomized trees," Machine learning, vol. 63, no. 1, pp. 3-42, 2006.
[22] Larson, Charles R., et al. "Interactions between auditory and somatosensory feedback for voice F 0 control." *Experimental Brain Research* 187.4 (2008): 613-621.
[23] Gómez-Vilda, Pedro, et al. "Characterizing neurological disease from voice quality biomechanical analysis." Cognitive Computation 5.4 (2013): 399-425.
[24] Gómez-Vilda, Pedro, et al. "Glottal source biometrical signature for voice pathology detection" *Speech Communication* 51.9 (2009): 759-781.
[25] "DIVA Source Code" DIVAsimulink7-6. Boston University. http://www.bu.edu/speechlab/software/diva-source-code/
[26] Guenther, Frank H., Satrajit S. Ghosh, and Jason A. Tourville. "Neural modeling and imaging of the cortical interactions underlying syllable production" *Brain and language* 96.3 (2006): 280-301.
[27] Ciccarelli, Gregory, Thomas Quatieri, Satrajit Ghosh. "Neruophysiological Vocal Source Modeling for biomarkers of Disease. In Interspeech 2016, to appear.
[28] Patel, Rupal, et al. ""The Caterpillar": A Novel Reading Passage for Assessment of Motor Speech Disorders." American Journal of Speech-Language Pathology 22.1 (2013): 1-9.
[29] Fairbanks, Grant, ed. Voice and articulation: Drillbook. Harper & Brothers, 1940.
[30] Darley, F. L., Aronson, A. E., Brown, J. R. (1975). Motor speech disorders. 3rd ed. Philadelphia, Pa. W.B. Saunders Company
[31] Van Riper, C. (1963). Speech correction. 4th ed. Englewoood Cliffs, N.J. Prentice Hall
[32] Aesop (2016) The North Wind and the Sun In. https://en.wikipedia.org/wiki/The_North_Wind_and_the_Sun
[33] Bishop, Christopher M. "Pattern recognition" Machine Learning 128 (2006)

What is claimed is:

1. A method of assessing a condition of a subject, the method comprising, in an automated system:
providing an electronically processed neurophysiological computational model of speech production having internal parameters;
providing a library relating the internal parameters to conditions of subjects;
receiving a speech related signal of the subject;
extracting speech features from the speech related signal of the subject;
electronically processing the neurophysiological computational model to predict speech features;
electronically comparing the extracted speech features to the predicted speech features from the neurophysiological computational model to obtain an error signal;
electronically inverting the error signal through an inverse of the neurophysiological computational model to update the internal parameters of the neurophysiological computational model; and
electronically processing the updated internal parameters of the neurophysiological computational model with respect to the library as biomarkers to identify a condition from the library; and
outputting the identified condition of the subject.

2. The method of claim 1 further comprising applying updated internal parameters to the neurophysiological computational model in multiple iterations of the steps of comparing, inverting and applying to obtain updated internal parameters to be processed.

3. The method of claim 1 further comprising performing an analysis of the updated internal parameters to extract features for assessing the subject.

4. The method of claim 1 wherein a correlation structure for the subject is extracted from the updated internal parameters in the step of processing.

5. The method of claim 1 wherein the extracted speech features and the predicted speech features include representations of vocal source.

6. The method of claim 1 wherein the extracted speech features and the predicted speech features include representations of vocal tract.

7. The method of claim 1 wherein the extracted speech features and the predicted speech features include time series representations.

8. The method of claim 1 wherein the subject is assessed for a neurological disorder.

9. The method of claim 1 wherein the subject is assessed for depression.

10. The method of claim 1 wherein the subject is assessed for Parkinson's disease.

11. The method of claim 1 wherein the subject is assessed for traumatic brain injury.

12. The method of claim 1 wherein the subject is assessed for the effects of cognitive stress.

13. The method of claim 1 wherein the neurophysiological computational model is a muscular control model and the internal parameters are control parameters.

14. An automated system for assessing a condition of a subject comprising a data processor including a non-transitory computer readable medium having stored thereon software that implements in the data processor:
receipt of a speech related signal of the subject and extraction of speech features from the speech related signal:
a forward neurophysiological computational model that responds to internal parameters to predict speech features;
an error generator that generates an error signal between the predicted speech features and speech features extracted from the speech related signal of the subject;
an inverse neurophysiological computational model that responds to the error signal to update the internal parameters to the forward neurophysiological computational model;
a library having data relating the internal parameters to conditions of subjects; and a disorder predictor that predicts a disorder for a subject based on the updated internal parameters of the neurophysiological computational model for the subject and the library data: and an output of the predicted disorder.

15. The system of claim 14 further comprising an analyzer that extracts features from the updated internal parameters to be processed by the disorder predictor.

16. The system of claim 14 further comprising a correlation structure extractor that extracts a correlation structure from the updated internal parameters.

17. The system of claim 14, wherein the forward neurophysiological computational model predicts representations of vocal source.

18. The system of claim 14 wherein the forward neurophysiological computational model predicts representations of vocal tract.

19. The system of claim 14 wherein the forward neurophysiological computational model predicts speech features that include time series representations.

20. The system of claim 14 wherein the neurophysiological computational model is a muscular control model and the internal parameters are control parameters.

21. A method of assessing a condition of a subject, the method comprising, in an automated system:
providing an electronically processed neurophysiological computational control model of speech production having control parameters;
providing a library relating the control parameters to conditions of subjects;
receiving a speech related signal of the subject;
extracting speech features from the speech related signal;
electronically processing the neurophysiological computational control model to predict speech features;
electronically comparing the extracted speech features to predicted speech features from the neurophysiological computational control model to obtain an error signal;
electronically inverting the error signal through an inverse of the neurophysiological computational control model to update the control parameters of the neurophysiological computational control model;
electronically processing the updated control parameters of the neurophysiological computational control model in a comparison with parameters associated with a disorder in the library to identify the disorder from the library; and
outputting an assessment of the subject based on the comparing step and the identified disorder.

22. An automated system for assessing a condition of a subject comprising a data processor including a non-transitory computer readable medium having stored thereon software that implements in the data processor:
an input receiving a speech related signal of a subject;
a forward control model that responds to control parameters to predict speech features;
an error generator that generates an error signal between the predicted speech features and speech features extracted from the speech related signal of the subject;
an inverse control model that responds to the error signal to update the control parameters of the forward control model;
a library storing data derived from updated control parameters of the forward control model in association with a disorder; and
a disorder predictor that predicts the disorder for the subject based on updated control parameters of the forward control model for the subject and the data stored in the library; and
an output of the predicted disorder.

* * * * *